US000001923H

United States Statutory Invention Registration [19]

[11] Reg. Number: H1,923

Theodoridis et al.

[45] Published: Nov. 7, 2000

[54] HERBICIDAL (OXAALKYL) PHENYL-SUBSTITUTED HETEROCYCLES

[75] Inventors: George Theodoridis, Princeton; Scott D. Crawford, Jackson; Lester L. Maravetz, Westfield, all of N.J.

[73] Assignee: FMC Corporation, Philadelphia, Pa.

[21] Appl. No.: 09/113,867

[22] Filed: Jul. 10, 1998

Related U.S. Application Data

[60] Provisional application No. 60/052,368, Jul. 11, 1997.

[51] Int. Cl.[7] ..... C07D 253/00

[52] U.S. Cl. ..... 549/182; 544/235; 544/312; 504/243; 504/299; 504/273; 504/282; 546/119; 548/263.2; 548/360.1; 548/366.1; 548/370.4; 548/452

[58] Field of Search ..... 504/299, 236, 504/243, 246, 273, 282, 285; 544/182, 235, 312, 314; 546/119; 548/251, 263.2, 360.1, 366.1, 452, 370.4

[56] References Cited

U.S. PATENT DOCUMENTS

| | | | |
|---|---|---|---|
| 5,116,404 | 5/1992 | Ishii et al. | 71/92 |
| 5,296,451 | 3/1994 | Rueb et al. | 504/236 |
| 5,519,022 | 5/1996 | Edwards et al. | 514/243 |
| 5,621,112 | 4/1997 | Ager et al. | 548/263.2 |
| 5,700,905 | 12/1997 | Schafer et al. | 544/309 |
| 5,817,814 | 10/1998 | Konz et al. | 544/309 |

FOREIGN PATENT DOCUMENTS

| | | |
|---|---|---|
| WO 90/02120 | 3/1990 | WIPO . |
| WO 95/32188 | 11/1995 | WIPO . |

*Primary Examiner*—Peter A. Nelson
*Attorney, Agent, or Firm*—Donald J. Silvert; I. Robert Silverman

[57] ABSTRACT

It has now been found that certain novel (oxaalkyl)phenyl-substituted heterocycles are useful as pre-emergent and post-emergent herbicides. These compounds are represented by formula I:

I

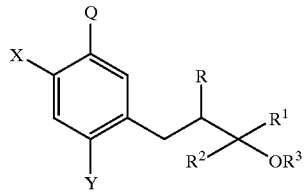

where Q is a heterocycle and X, Y, R, $R^1$, $R^2$, and $R^3$ are substituents as described in the specification. Preferred are those compounds where Y and R are chloro; $R^1$ and $R^2$ are hydrogen or methyl; $R^3$ is hydrogen or alkylaminocarbonyl; X is fluorine; and Q is a 1-substituted-6-trifluoromethyl-2, 4(1H,3H)-pyrimidinedion-3-yl.

18 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

HERBICIDAL (OXAALKYL) PHENYL-SUBSTITUTED HETEROCYCLES

This application claims benefit to provisional application Ser. No. 60/052,368 filed Jul. 11, 1997.

BACKGROUND OF THE INVENTION

This invention relates generally to novel herbicidal compounds and methods for their use in controlling unwanted plant species in agriculture. In particular, it pertains to herbicidal (oxaalkyl)phenyl-substituted heterocycles, and more particularly it pertains to herbicidal (oxaalkyl)phenyl-substituted heterocycles where the oxaalkyl moiety of the (oxaalkyl)phenyl is substituted and the heterocycle is a 1-substituted-6-trifluoromethyl-2,4(1H,3H)-pyrimidinedion-3-yl, a 4-difluoromethyl-4,5-dihydro-3-methyl-1,2,4-triazol-5(1H)-on-1-yl, a 4-halo-5-difluoromethoxy-1-methylpyrazol-3-yl, a 3,4,5,6-tetrahydrophthalimid-1-yl, a 1,4-dihydro-4-(3-fluoropropyl)-5H-tetrazole-5-on-1-yl, a 3-chloro-4,5,6,7-tetrahydroindazol-2-yl, a 5,6,7,8-tetrahydro-1,2,4-triazolo[4,3-A]pyridin-3(2H)-on-2-yl, 5,6,7,8-tetrahydro-1H,3H-[1,3,4]thiadiazolo[3,4-a]pyridazineimin-1-yl or a 4-methyl-1,2,4-triazine-3,5-dion-2-yl moiety.

There is a continuing demand for new herbicides. Herbicides are useful for controlling unwanted vegetation which may otherwise cause significant damage to crops such as wheat, corn, soybeans and cotton, to name a few. For crop protection, so-called "selective" herbicides are desired which can control the weeds without damaging the crop. Such crops are said to exhibit tolerance to the herbicide. In certain other situations, it is desirable to use herbicides that provide complete vegetation control such as in areas around railroad tracks and other structures. While many commercial products are available that provide selective or complete vegetation control, the demand exists for new, safe herbicides that are more effective and less costly.

German Offenlegungsschrift DE 4237920A1 (Ciba-Geigy AG) describes herbicidally active compounds of the following formula:

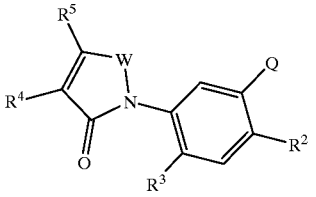

among which are compounds where W is $N(R^1)C{=}O$; $R^1$ is $C_1$–$C_4$-alkyl, $C_1$–$C_4$-haloalkyl, $C_1$–$C_4$-alkenyl, or $C_1$–$C_4$-alkynyl; $R^2$ is halogen or cyano; $R^3$ is hydrogen or halogen; $R^4$ is hydrogen or $C_1$–$C_4$-alkyl; $R^5$ is $C_1$–$C_4$-alkyl or $C_1$–$C_4$-haloalkyl; and Q is $CR^6R^7R^8$ where $R^6$ and $R^7$ are hydrogen or alkyl; and $R^8$ is $X_1R^9$ where $X_1$ is oxygen; $R^9$ is hydrogen or $C({=}X_2)R^{10}$ where $X_2$ is oxygen; and $R^{10}$ is $C_1$–$C_5$-alkyl or $C_1$–$C_4$-alkoxy.

British Patent GB 2,289,893 (BASF Akt.) describes herbicidally active compounds of the following formula:

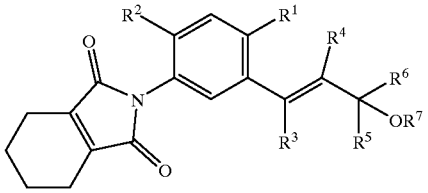

among which are compounds where $R^1$ is halogen or cyano; $R^2$ is hydrogen or halogen; $R^3$, $R^4$ are hydrogen, halogen, or alkyl; $R^5$, $R^6$ are hydrogen or alkyl; and $R^7$ is hydrogen, alkylcarbonyl, alkoxycarbonyl, alkylaminocarbonyl, or cycloalkylaminocarbonyl.

SUMMARY OF THE INVENTION

It has now been found that certain novel (oxaalkyl) phenyl-substituted heterocycles are useful as pre-emergent and post-emergent herbicides. These compounds are represented by formula I:

I

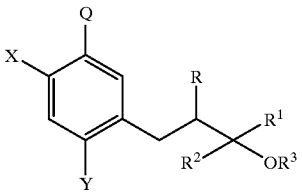

where Q is a heterocycle, and X, Y, R, $R^1$, $R^2$, and $R^3$ are substituents as described below. Preferred compounds include those where Y and R are chloro; $R^1$ and $R^2$ are hydrogen or methyl; $R^3$ is hydrogen or alkylaminocarbonyl; X is fluorine; and Q is a 1-substituted-6-trifluoromethyl-2,4(1H,3H)-pyrimidinedion-3-yl.

DETAILED DESCRIPTION OF THE INVENTION

Certain novel (oxaalkyl)phenyl-substituted heterocycles are useful as pre-emergent and post-emergent herbicides. These compounds are represented by formula I:

I

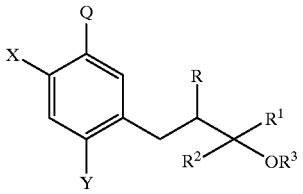

where Q is

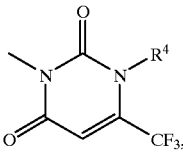

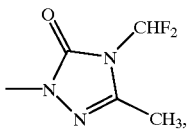

-continued

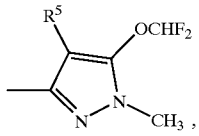

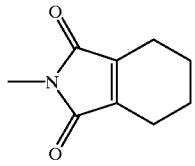

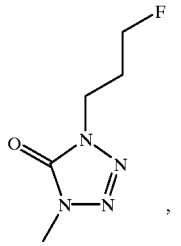

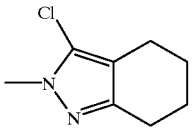

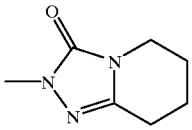

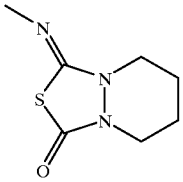

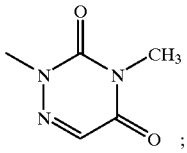

R is hydrogen, halogen, or alkyl;

$R^1$ is hydrogen, cyano, or alkyl;

$R^2$ is hydrogen, or alkyl;

$R^3$ is hydrogen, straight or branched chain alkyl carbonyl, alkoxycarbonyl, alkylaminocarbonyl, or cycloalkylaminocarbonyl;

X is hydrogen or halogen;

Y is halogen, cyano, alkyl, haloalkyl, alkoxy, haloalkoxy, or nitro;

$R^4$ is hydrogen, amino, straight or branched chain alkyl, haloalkyl, cyanoalkyl, alkoxyalkyl, arylalkyl, alkoxycarbonylalkyl, arylalkyl, alkoxycarbonylalkyl, alkenyl, alkynyl, or a salt-forming ion; and $R^5$ is halogen.

For Q in formula I, the above structural moieties may also be identified by their chemical name as follows:

A

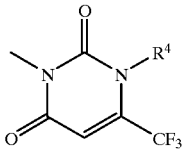

B

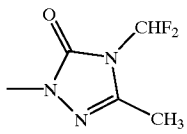

-continued

C

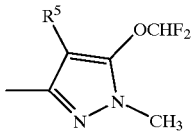

D

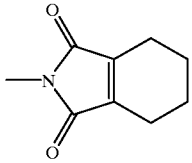

E

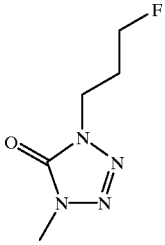

F

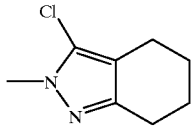

G

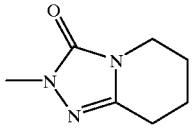

H

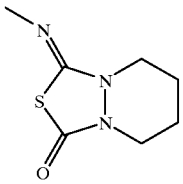

J

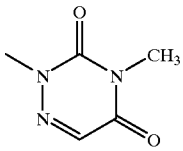

where "A" is 1-substituted-6-trifluoromethyl-2,4(1H,3H)-pyrimidinedion-3-yl, "B" is 4-difluoromethyl-4,5-dihydro-3-methyl-1,2,4-triazol-5(1H)-on-1-yl, "C" is 4-halo-5-difluoromethoxy-1-methylpyrazol-3-yl, "D" is 3,4,5,6-tetrahydrophthalimid-1-yl, "E" is 1,4-dihydro-4-(3-fluoropropyl)-5H-tetrazole-5-on-1-yl, "F" is 3-chloro-4,5,6,7-tetrahydroindazol-2-yl, "G" is 5,6,7,8-tetrahydro-1,2,4-triazolo[4,3-A]pyridin-3(2H)-on-2-yl, "H" is 5,6,7,8-tetrahydro-1H,3H-[1,3,4]thiadiazolo[3,4-a]pyridazineimin-1-yl, and "J" is 4-methyl-1,2,4-triazine-3,5-dion-2-yl.

One aspect of this invention relates to compounds of formula I where Q is 1-substituted-6-trifluoromethyl-2,4(1H,3H)-pyrimidinedion-3-yl and R, $R^1$, $R^2$, $R^3$, X, Y, and $R^4$ are as described above.

Another aspect of this invention relates to compounds of formula I where Q is 4-difluoromethyl-4,5-dihydro-3-methyl-1,2,4-triazol-5(1H)-on-1-yl and R, $R^1$, $R^2$, $R^3$, X, and Y are as described above.

Another aspect of this invention relates to compounds of formula I where Q is 4-halo-5-difluoromethoxy-1-methylpyrazol-3-yl and R, $R^1$, $R^2$, $R^3$, X, Y, and $R^5$ are as described above.

Another aspect of this invention relates to compounds of formula I where Q is 3,4,5,6-tetrahydrophthalimid-1-yl and R, $R^1$, $R^2$, $R^3$, X, and Y are as described above.

Another aspect of this invention relates to compounds of formula I where Q is 1,4-dihydro-4-(3-fluoropropyl)-5H-tetrazole-5-on-1-yl and R, $R^1$, $R^2$, $R^3$, X, and Y are as described above.

Another aspect of this invention relates to compounds of formula I where Q is 3-chloro-4,5,6,7-tetrahydroindazol-2-yl and R, $R^1$, $R^2$, $R^3$, X, and Y are as described above.

Another aspect of this invention relates to compounds of formula I where Q is 5,6,7,8-tetrahydro-1,2,4-triazolo[4,3-A]pyridin-3(2H)-on-2-yl and R, $R^1$, $R^2$, $R^3$, X, and Y are as described above.

Another aspect of this invention relates to compounds of formula I where Q is 5,6,7,8-tetrahydro-1H,3H-[1,3,4]thiadiazolo[3,4-a]pyridazineimin-1-yl and R, $R^1$, $R^2$, $R^3$, X, and Y are as described above.

Another aspect of this invention relates to compounds of formula I where Q is 4-methyl-1,2,4-triazine-3,5-dion-2-yl and R, $R^1$, $R^2$, $R^3$, X, and Y are as described above.

Preferred are those of formula I where Y and R are chloro; $R^1$ and $R^2$ are hydrogen or methyl; $R^3$ is hydrogen or alkylaminocarbonyl; and X is fluoro.

Particularly preferred are those compounds of formula I where Q is 1-substituted-6-trifluoromethyl-2,4(1H,3H)-pyrimidinedion-3-yl; Y and R are chloro; $R^1$ and $R^2$ are hydrogen or methyl; $R^3$ is hydrogen or methylaminocarbonyl; X is fluoro; and $R^4$ is methyl or amino.

As used in this specification and unless otherwise indicated the terms "alkyl", "alkenyl", "alkynyl", used alone or as part of a larger moiety includes 1 to 6 carbon atoms, and the term "cycloalkyl" includes 3 to 8 carbon atoms. "Halogen" refers to fluorine, bromine, or chlorine. "Salt-forming ion" refers to sodium, potassium, lithium, barium or calcium.

The (oxaalkyl)phenyl-substituted heterocycles of formula I may be prepared by the methods described below or by methods similar to those known to one skilled in the art for similar compounds.

Scheme 1

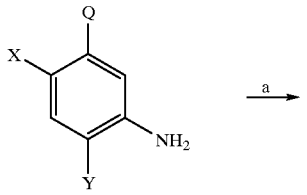

1

-continued

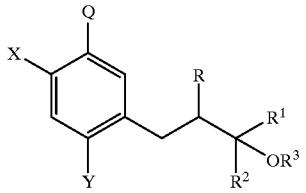

I

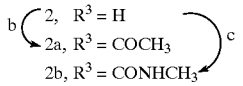

(a) $HC{=}CR^1R^2OH$, t-BuONO, Cu(II)Cl, $CH_3CN$ (b) $Ac_2O$, DMAP, $CH_2Cl_2$ (c) $CH_3NCO$, dibutyltin diacetate, $CH_2Cl_2$ Scheme 1 above illustrates a general procedure for preparing compounds of formula I where R is chloro, and $R^1$ and $R^2$ are hydrogen or alkyl. The starting aniline 1 may be prepared according to known methods, such as those taught in U.S. Pat. Nos. 5,041,155, 4,954,159, or 4,932,996. Diazotization of 1 and reaction with an appropriate alkenyl alcohol as shown in step (a) affords the alcohol 2. Alcohol 2 may be acylated with an appropriate anhydride according to step (b) to provide 2a or converted with an isocyanate according to step (c) to provide carbamate 2b.

Procedures for some of the methods that are useful to prepare compounds of this invention are given in the Examples below.

EXAMPLE 1

2-CHLORO-3-METHYL-1-[2-CHLORO-4-FLUORO-5-[1-METHYL-6-TRIFLUOROMETHYL-2,4(1H,3H)-PYRIMIDINDION-3-YL]PHENYL]BUTAN-3-OL (Compound 1)

A mixture of 2.0 grams (0.015 mole) of copper(II) chloride, and 1.5 grams (0.015 mole) of tert.-butyl nitrite in 10.2 mL (0.10 mole) of 2-methyl-3-buten-2-ol was rapidly stirred, and a solution of 2.9 grams (0.010 mole) of 1-methyl-6-trifluoromethyl-3-(5-amino-4-chloro-2-fluorophenyl)-2,4(1H,3H)pyrimidinedione in 80 mL of acetonitrile was added slowly. Upon completion of addition, the reaction mixture was stirred for about one hour, then it was poured into water. The mixture was extracted with diethyl ether, and the extract was dried with magnesium sulfate. The extract was filtered, and the filtrate was concentrated under reduced pressure to a residue. The residue was purified by column chormatography on silica gel using ethyl acetate in methylene chloride, yielding 3.8 grams of Compound 1. The NMR spectrum was consistent with the proposed structure.

EXAMPLE 2

2-CHLORO-3-METHYL-1-[2-CHLORO-4-FLUORO-5-[1-METHYL-6-TRIFLUOROMETHYL-2,4(1H,3H)-PYRIMIDINDION-3-YL]PHENYL]BUTAN-3-YL ACETATE (Compound 16)

A mixture of 0.95 gram (0.0021 mole) of 2-chloro-3-methyl-1-[2chloro-4-fluoro-5-[1-methyl-6-trifluoromethyl-2,4(1H,3H)-pyrimidindion-3-yl]phenyl]butan-3-ol, 0.26 gram (0.0026 mole) of acetic anhydride, and 0.39 gram (0.0032 mole) of 4-dimethylaminopyridine in 5 mL of methylene chloride was stirred at ambient temperature for about 18 hours. The reaction mixture was then diluted with water and extracted with three 45 mL portions of ethyl acetate. The combined extracts were dried with magnesium sulfate and filtered. The filtrate was concentrated under reduced pressure to a residue. The residue was purified by column chormatography on silica gel using ethyl acetate in heptane, yielding 0.66 gram of Compound 16, mp 40–50° C. The NMR spectrum was consistent with the proposed structure.

EXAMPLE 3

2-CHLORO-1-[2-CHLORO-4-FLUORO-5-[4DIFLUOROMETHYL-4,5-DIHYDRO-3-METHYL-1,2,4-TRIAZOL-5(1H)-ON-1-YL]PHENYL]PROPAN-3-YL METHYLCARBAMATE (Compound 31)

A solution of 0.50 gram (0.0013 mole) of 2-chloro-1-[2-chloro-fluoro-5-[4-difluoromethyl-4,5-dihydro-3-methyl-1,2,4-triazol-5(1H)-on-1-yl]phenyl]propan-3-ol (prepared in the manner of Example 1), 0.23 gram (0.0040 mole) of methyl isocyanate, and two drops of dibutyltin diacetate in about 20 mL of methylene chloride was stirred at ambient temperature for 18 hours. The crude product was purified by column chormatography on silica gel using ethyl acetate in methylene chloride, yielding 0.43 gram of Compound 31. The NMR spectrum was consistent with the proposed structure.

Table 1 below shows representative compounds of the present invention.

TABLE 1

Herbicidal (oxaalkyl)phenyl-substituted heterocycles

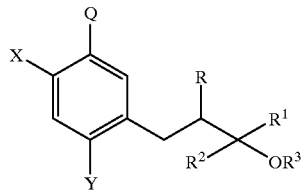

where Q is one of the following moieties:

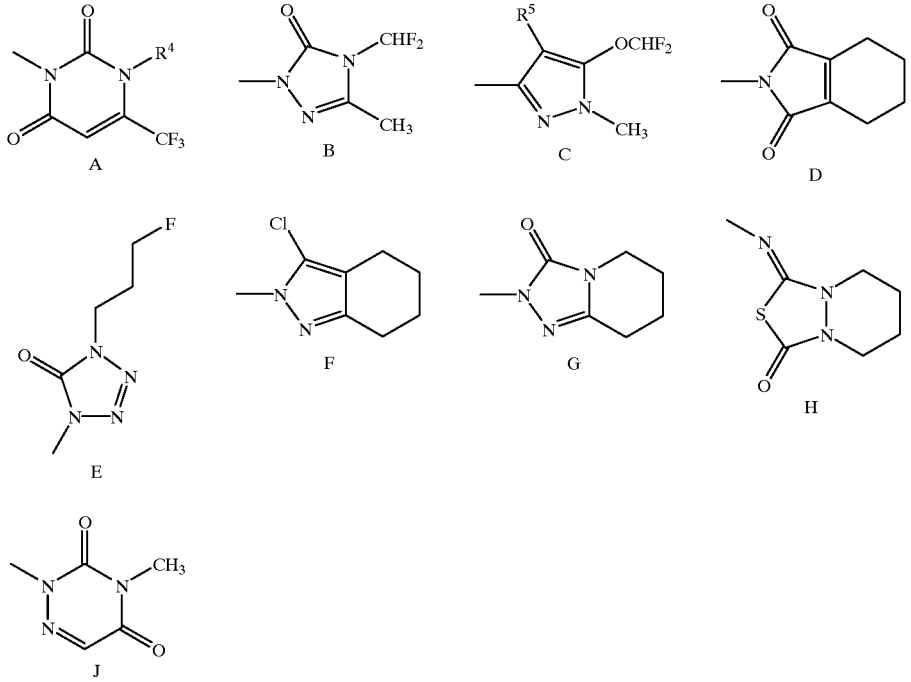

Cmpd

TABLE 1-continued

| No. | R | $R^1$ | $R^2$ | $R^3$ | X | Y | Q | $R^4$ or $R^5$ |
|---|---|---|---|---|---|---|---|---|
| 1 | Cl | $CH_3$ | $CH_3$ | H | F | Cl | A | $CH_3$ |
| 2 | Cl | $CH_3$ | $CH_3$ | H | F | Cl | B | — |
| 3 | Cl | $CH_3$ | $CH_3$ | H | F | Cl | C | Cl |
| 4 | H | $CH_3$ | $CH_3$ | H | H | Cl | A | $CH_3$ |
| 5 | Cl | $CH_3$ | $CH_3$ | H | H | Cl | A | $CH_3$ |
| 6 | Br | $CH_3$ | $CH_3$ | H | H | Cl | A | $CH_3$ |
| 7 | Br | $CH_3$ | $CH_3$ | H | F | Cl | A | $CH_3$ |
| 8 | Cl | $CH_3$ | $CH_3$ | H | F | Br | A | $CH_3$ |
| 9 | Cl | $CH_3$ | $CH_3$ | H | F | C≡N | A | $CH_3$ |
| 10 | H | $CH_3$ | $CH_3$ | H | F | Cl | A | $CH_3$ |
| 11 | $CH_3$ | $CH_3$ | $CH_3$ | H | F | Cl | A | $CH_3$ |
| 12 | Cl | $C_2H_5$ | $CH_3$ | H | F | Cl | A | $CH_3$ |
| 13 | Cl | C≡N | —$CH_3$ | H | F | Cl | A | $CH_3$ |
| 14 | Cl | $CH_3$ | $CH_3$ | H | F | C≡N | A | $NH_2$ |
| 15 | Cl | $CH_3$ | $CH_3$ | H | F | C≡N | B | — |
| 16 | Cl | $CH_3$ | $CH_3$ | $COCH_3$ | F | Cl | A | $CH_3$ |
| 17 | Cl | $CH_3$ | $CH_3$ | $COCH_3$ | F | Cl | B | — |
| 18 | Cl | $CH_3$ | $CH_3$ | $COCH_3$ | F | Cl | C | Cl |
| 19 | Cl | H | $CH_3$ | H | F | Cl | A | $CH_3$ |
| 20 | Cl | H | H | H | F | Cl | A | $CH_3$ |
| 21 | Cl | H | H | $COCH_3$ | F | Cl | A | $CH_3$ |
| 22 | Cl | H | H | H | F | Cl | A | $NH_2$ |
| 23 | Cl | H | H | $COCH_3$ | F | Cl | A | $NH_2$ |
| 24 | Cl | H | H | H | F | Cl | B | — |
| 25 | Cl | $CH_3$ | $CH_3$ | H | F | Cl | D | — |
| 26 | Cl | $CH_3$ | $CH_3$ | H | F | Cl | C | Br |
| 27 | Cl | $CH_3$ | $CH_3$ | $COCH_3$ | F | Cl | C | Br |
| 28 | Cl | H | H | $CONHCH_3$ | F | Cl | A | $CH_3$ |
| 29 | Cl | H | H | $CONHCH(CH_3)_2$ | F | Cl | A | $CH_3$ |
| 30 | Cl | H | H | $CO_2CH_3$ | F | Cl | A | $CH_3$ |
| 31 | Cl | H | H | $CONHCH_3$ | F | Cl | B | — |
| 32 | Cl | H | H | $CONHC_2H_5$ | F | Cl | B | — |
| 33 | Cl | H | H | $CONHC(CH_3)_3$ | F | Cl | B | — |
| 34 | Cl | H | H | $CONHCH(CH_3)_2$ | F | Cl | B | — |
| 35 | Cl | H | H | CONH-cyclohexyl | F | Cl | B | — |
| 36 | Cl | H | H | $CONH(CH_2)_5CH_3$ | F | Cl | B | — |
| 37 | Cl | $CH_3$ | $CH_3$ | H | Cl | Cl | B | — |
| 38 | Cl | $CH_3$ | $CH_3$ | H | F | Cl | E | — |
| 39 | Cl | $CH_3$ | $CH_3$ | $CONHCH_3$ | F | Cl | E | — |
| 40 | Cl | H | H | H | F | Cl | E | — |
| 41 | Cl | $CH_3$ | $CH_3$ | $COCH_3$ | F | Cl | E | — |
| 42 | Cl | $CH_3$ | $CH_3$ | H | F | Cl | F | — |
| 43 | Cl | H | H | $COCH_3$ | F | Cl | F | — |
| 44 | Cl | H | H | H | Cl | Cl | F | — |
| 45 | Cl | H | H | H | F | Cl | G | — |
| 46 | Cl | $CH_3$ | $CH_3$ | $COCH_3$ | F | Cl | G | — |
| 47 | Cl | H | H | H | F | Cl | H | — |
| 48 | H | H | H | H | F | Cl | J | — |
| 49 | Cl | $CH_3$ | $CH_3$ | H | F | Cl | J | — |
| 50 | $CH_3$ | $CH_3$ | $CH_3$ | H | Cl | Cl | J | — |
| 51 | Cl | $CH_3$ | $CH_3$ | H | F | Cl | A | H |
| 52 | Cl | $CH_3$ | $CH_3$ | H | F | Cl | A | $C_2H_5$ |
| 53 | Cl | $CH_3$ | $CH_3$ | H | F | Cl | A | n-$C_3H_7$ |
| 54 | Cl | $CH_3$ | $CH_3$ | H | F | Cl | A | $CH(CH_3)_2$ |
| 55 | Cl | $CH_3$ | $CH_3$ | H | F | Cl | A | $CH_2CN$ |
| 56 | Cl | $CH_3$ | $CH_3$ | H | F | Cl | A | $CH_2C_6H_5$ |
| 57 | Cl | $CH_3$ | $CH_3$ | H | F | Cl | A | $CH_2C{\equiv}CH$ |
| 58 | Cl | $CH_3$ | $CH_3$ | H | F | Cl | A | $CH_2OCH_3$ |
| 59 | Cl | $CH_3$ | $CH_3$ | H | F | Cl | A | $CH_2CO_2C_2H_5$ |
| 60 | Cl | $CH_3$ | $CH_3$ | H | F | Cl | A | $CH_2CH{=}CH_2$ |
| 61 | Cl | $CH_3$ | $CH_3$ | H | F | Cl | A | $NH_2$ |
| 62 | Cl | $CH_3$ | $CH_3$ | H | F | Cl | A | $CHF_2$ |
| 63 | Cl | $CH_3$ | $CH_3$ | H | F | Cl | A | Na |
| 64 | Cl | $CH_3$ | $CH_3$ | H | F | Cl | A | $CH_2CH_2CH_2F$ |
| 65 | Cl | $CH_3$ | $CH_3$ | H | F | $CH_3$ | A | $CH_3$ |
| 66 | Cl | $CH_3$ | $CH_3$ | H | F | $CF_3$ | A | $CH_3$ |
| 67 | Cl | $CH_3$ | $CH_3$ | H | F | $OCHF_2$ | A | $CH_3$ |
| 68 | Cl | $CH_3$ | $CH_3$ | H | F | $NO_2$ | A | $CH_3$ |
| 69 | Cl | $CH_3$ | $CH_3$ | H | F | $OCH_3$ | A | $CH_3$ |

TABLE 2

Characterizing Data

| Cmpd No | Melting Point °C. Physical State | Cmpd No | Melting Point °C. Physical State |
|---|---|---|---|
| 1 | 132–135 | 31 | 136–137 |
| 2 | OIL | 32 | 119–120 |
| 3 | OIL | 33 | OIL |
| 16 | 40–50 SOFTENS | 34 | 101–102 |
| 17 | OIL | 35 | 125–126 |
| 18 | OIL | 36 | 71–73 |
| 24 | OIL | 37 | OIL |

Biological Testing

The (oxaalkyl)phenyl-substituted heterocycles of this invention were tested for pre- and postemergence herbicidal activity using a variety of crops and weeds. The test plants included soybean (*Glycine max* var. Winchester), field corn (*Zea mays* var. Pioneer 3732), wheat (*Triticum aestivum* var. Lew), morningglory (*Ipomea lacunosa* or *Ipomea hederacea*), leaf (*Abutilon theophrasti*), green foxtail (*Setaria viridis*), Johnsongrass (*Sorghum halepense*), blackgrass (*Aloepecurus myosuroides*), common chickweed (*Stellaria media*), and common cocklebur (*Xanthium strumarium* L.).

For preemergence testing, two disposable fiber flats (8 cm×15 cm×25 cm) for each rate of application of each candidate herbicide were filled to an approximate depth of 6.5 cm with steam-sterilized sandy loam soil. The soil was leveled and impressed with a template to provide five evenly spaced furrows 13 cm long and 0.5 cm deep in each flat. Seeds of soybean, wheat, corn, green foxtail, and johnsongrass were planted in the furrows of the first flat, and seeds of velvetleaf, morningglory, common chickweed, cocklebur, and blackgrass were planted in the furrows of the second flat. The five-row template was employed to firmly press the seeds into place. A topping soil of equal portions of sand and sandy loam soil was placed uniformly on top of each flat to a depth of approximately 0.5 cm. Flats for postemergence testing were prepared in the same manner except that they were planted 9–14 days prior to the preemergence flats and were placed in a greenhouse and watered, thus allowing the seeds to germinate and the foliage to develop.

In both pre- and postemergence tests, a stock solution of the candidate herbicide was prepared by dissolving 0.27 g of the compound in 20 mL of water/acetone (50/50) containing 0.5% v/v sorbitan monolaurate. For an application rate of 3000 g/ha of herbicide a 10 mL portion of the stock solution was diluted with water/acetone (50/50) to 45 mL. The volumes of stock solution and diluent used to prepare solutions for lower application rates are shown in the following table:

| Application Rate (g/ha) | Volume of Stock Solution (mL) | Volume of Acetone/Water (mL) | Total Volume of Spray Solution (mL) |
|---|---|---|---|
| 3000 | 10 | 35 | 45 |
| 1000 | 3 | 42 | 45 |
| 300 | 1 | 44 | 45 |
| 100 | 0.3 | 45 | 45.3 |
| 30 | 0.1 | 45 | 45.1 |
| 10 | 0.03 | 45 | 45.03 |
| 3 | 0.01 | 45 | 45.01 |

The preemergence flats were initially subjected to a light water spray. The four flats were placed two by two along a conveyor belt (i.e., the two preemergence followed by the two postemergence flats). The conveyor belt fed under a spray nozzle mounted about ten inches above the postemergent foliage. The preemergent flats were elevated on the belt so that the soil surface was at the same level below the spray nozzle as the foliage canopy of the postemergent plants. The spray of herbicidal solution was commenced and once stabilized, the flats were passed under the spray at a speed to receive a coverage equivalent of 1000 L/ha. At this coverage the application rates are those shown in the above table for the individual herbicidal solutions. The preemergence flats were watered immediately thereafter, placed in the greenhouse and watered regularly at the soil surface. The postemergence flats were immediately placed in the greenhouse and not watered until 24 hours after treatment with the test solution. Thereafter they were regularly watered at ground level. After 12–17 days the plants were examined and the phytotoxicity data were recorded.

Herbicidal activity data at selected application rates are given for various components of this invention in Table 3 and Table 4. The test compounds are identified by numbers which correspond to those in Table 1.

Phytotoxicity data were taken as percent control. Percent control was by a method similar to the 0 to 1 00 rating system disclosed in "Research Methods in Weed Science," 2nd ed., B. Truelove, Ed.; Southern Weed Science Society; Auburn University, Auburn, Ala., 1977. The rating system is as follows:

Herbicide Rating System

| Rating Percent Control | Description of Main Categories | Crop Description | Weed Description |
|---|---|---|---|
| 0 | No effect | No crop reduction or injury | No weed control |
| 10 | Slight effect | Slight discoloration or stunting | Very poor weed control |
| 20 | | Some discoloration, stunting or stand loss | Poor weed control |
| 30 | | Crop injury more pronounced but not lasting | Poor to deficient weed control |
| 40 | Moderate effect | Moderate injury, crop usually recovers | Deficient weed control |
| 50 | | Crop injury more lasting, recovery doubtful | Deficient to moderate weed control |
| 60 | | Lasting crop injury, no recovery | Moderate weed control |
| 70 | Severe | Heavy injury and stand loss | Control somewhat less than satisfactory |
| 80 | | Crop nearly destroyed, a few survivors | Satisfactory to good weed control |
| 90 | | Only occasional live plants left | Very good to excellent control |

-continued

Herbicide Rating System

| Rating Percent Control | Description of Main Categories | Crop Description | Weed Description |
|---|---|---|---|
| 100 | Complete effect | Complete crop destruction | Complete destruction |

The compounds of the present invention were tested in the laboratory as water/acetone (50/50) solutions containing 0.5% v/v sorbitan monolaurate emulsifier. It is expected that all formulations normally employed in applications of herbicides would be usable with the compounds of the present invention. These include wettable powders, emulsifiable concentrates, water suspensions, flowable concentrates, and the like. The pre- and post-emergence activity of selected compounds is shown in Tables 3 and 4.

TABLE 3

PREEMERGENCE HERBICIDAL ACTIVITY (% CONTROL)

| Cmp No | SOY | WHT | CRN | ABUTH | IPOSS | STEME | XANPE | ALOMY | SETVI | SORHA |
|---|---|---|---|---|---|---|---|---|---|---|
| 1 | 100 | 80 | 95 | 100 | 100 | 100 | 95 | 80 | 100 | 95 |
| 2 | 60 | 70 | 80 | 100 | 100 | 90 | 60 | 70 | 100 | 90 |
| 3 | 60 | 30 | 40 | 100 | 100 | 100 | 100 | ND | 100 | 75 |
| 16 | 100 | 70 | 90 | 100 | 100 | 100 | 100 | ND | 100 | 100 |
| 17 | 70 | 50 | 85 | 100 | 100 | 95 | 80 | ND | 80 | 100 |
| 18 | 70 | 20 | 20 | 100 | 100 | 100 | 60 | ND | 100 | 80 |
| 24 | 30 | 50 | 70 | 100 | 100 | ND | 95 | 10 | 100 | 65 |
| 31 | 100 | 70 | 90 | 100 | 100 | 100 | ND | 70 | 100 | 100 |
| 32 | 100 | 40 | 70 | 100 | 95 | 90 | ND | 75 | 100 | 95 |
| 33 | 60 | 20 | 80 | 100 | 70 | 90 | ND | 70 | 100 | 80 |
| 34 | 80 | 50 | 70 | 100 | 100 | 100 | ND | 60 | 100 | 100 |
| 35 | 30 | 20 | 10 | 100 | 90 | 100 | ND | 30 | 100 | 50 |
| 36 | 70 | 30 | 30 | 100 | 100 | 60 | ND | 50 | 100 | 70 |

TABLE 4

POSTEMERGENCE HERBICIDAL ACTIVITY (% CONTROL)

| Cmp No | SOY | WHT | CRN | ABUTH | IPOSS | STEME | XANPE | ALOMY | SETVI | SORHA |
|---|---|---|---|---|---|---|---|---|---|---|
| 1 | 100 | 90 | 100 | 100 | 100 | 100 | 100 | 80 | 100 | 100 |
| 2 | 80 | 60 | 80 | 100 | 100 | 70 | 55 | 70 | 80 | 80 |
| 3 | 95 | 40 | 70 | 100 | 100 | 100 | 100 | ND | 100 | 60 |
| 16 | 95 | 60 | 90 | 100 | 90 | 100 | 100 | 100 | 100 | 100 |
| 17 | 80 | 50 | 90 | 100 | 100 | 100 | 60 | 80 | 100 | 100 |
| 18 | 80 | 40 | 75 | 100 | 100 | 100 | 90 | 80 | 100 | 80 |
| 24 | 80 | 30 | 80 | 100 | 100 | 10 | 100 | 30 | 80 | 80 |
| 31 | 95 | 50 | 85 | 100 | 100 | 100 | 100 | 75 | 100 | 100 |
| 32 | 95 | 40 | 80 | 100 | 95 | 100 | 100 | 70 | 100 | 90 |
| 33 | 90 | 40 | 80 | 100 | 100 | 80 | 100 | 60 | 100 | 80 |
| 34 | 90 | 50 | 85 | 100 | 90 | 75 | 100 | 65 | 100 | 95 |
| 35 | 80 | 25 | 70 | 100 | 80 | 30 | 100 | 30 | 80 | 60 |
| 36 | 80 | 30 | 80 | 100 | 100 | 100 | 100 | 50 | 80 | 75 |

Rate of Application is 0.3 Kg/Ha
SOY is soybean, WHT is wheat, CRN is corn, ABUTH is velvetleaf, IPOSS is morningglory, STEMME is chickweed, XANPE is cocklebur, ALOMY is blackgrass, SETVI is green foxtail, and SORHA is johnsongrass
ND is no data Herbicidal compositions are prepared by combining herbicidally effective amounts of the active compounds with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application. It is to be understood that the amounts specified in this specification are intended to be approximate only, as if the word "about" were placed in front of the amounts specified.

These herbicidal compositions may be applied either as water-diluted sprays, or dusts, or granules to the areas in which suppression of vegetation is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders, also useful formulations for both pre- and post-emergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5–80% of active ingredient, depending on the absorbency of the carrier, and usually also contain a small amount of a wetting, dispersing or emulsifying agent to facilitate dispersion. For example, a useful wettable powder formulation contains 80.0 parts of the herbicidal compound, 17.9 parts of Palmetto clay, and 1.0 part of sodium lignosulfonate and 0.3 part of sulfonated aliphatic polyester as wetting agents. Additional wetting agent and/or oil will frequently be added to the tank mix for postemergence application to facilitate dispersion on the foliage and absorption by the plant.

Other useful formulations for herbicidal applications are emulsifiable concentrates (ECs) which are homogeneous liquid compositions dispersible in water or other dispersant, and may consist entirely of the herbicidal compound and a liquid or solid emulsifying agent, or may also contain a liquid carrier, such as xylene, heavy aromatic naphthas, isphorone, or other non-volatile organic solvents. For herbicidal application these concentrates are dispersed in water or other liquid carrier and normally applied as a spray to the area to be treated. The percentage by weight of the essential active ingredient may vary according to the manner in which the composition is to be applied, but in general comprises 0.5 to 95% of active ingredient by weight of the herbicidal composition.

Flowable formulations are similar to ECs except that the active ingredient is suspended in a liquid carrier, generally water. Flowables, like ECs, may include a small amount of a surfactant, and will typically contain active ingredients in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of longChain mercaptans and ethylene oxide. Many other types of useful surface-active agents are available in commerce. Surface-active agents, when used, normally comprise 1 to 15% by weight of the composition.

Other useful formulations include suspensions of the active ingredient in a relatively non-volatile solvent such as water, corn oil, kerosene, propylene glycol, or other suitable solvents.

Still other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relative coarse particles, are of particular utility for aerial distribution or for penetration of cover crop canopy. Pressurized sprays, typically aerosols wherein the active ingredient is dispersed in finely divided form as a result of vaporization of a low-boiling dispersant solvent carrier, such as the Freon fluorinated hydrocarbons, may also be used. Water-soluble or water-dispersible granules are free-flowing, non-dusty, and readily water-soluble or water-miscible. The soluble or dispersible granular formulations described in U.S. Pat. No. 3,920,442 are useful herein with the present herbicidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed. The compounds may be applied as preemergent or postemergent herbicides, with postemergent application preferred. For field use, where there are losses of herbicide, application rates may be in the range of 10 to 300 grams per hectare and are preferably in the range of 30 to 125 g/ha. The compounds of this invention are also useful as cotton defoliation and potato dessication agents. Such agents aid in the harvesting of the cotton and potato crops.

The active herbicidal compounds of the present invention may also be used in combination with other herbicides. Such herbicides include, for example: N-(phosphonomethyl) glycine, isopropylamine salt ("glyphosate"); aryloxyalkanoic acids such as (2,4-dichlorophenoxy)acetic acid ("2,4-D"), (4-chloro-2-methylphenoxy)acetic acid ("MCPA"), (+/−)-2-(4chloro-2-methylphenoxy)propanoic acid ("MCPP"); ureas such as N,N-dimethyl-N'-[4-(1-methylethyl)phenyl]urea ("isoproturon"); imidazolinones such as 2-[4,5-dihydro-4-methyl-4-(1-methylethyl)-5-oxo-1H-imidazol-2-yl]-3-pyridinecarboxylic acid ("imazapyr"), a reaction product comprising (+/−)-2-[4,5-dihydro-4-methyl-4-(1-methylethyl)-5-oxo-1H-imidazol-2-yl]-4-methylbenzoic acid and (+/−)2-[4,5-dihydro-4-methyl-4-(1-methylethyl)-5-oxo-1H-imidazol-2-yl]-5-methylbenzoic acid ("imazamethabenz"), (+/−)-2-[4,5-dihydro-4-methyl-4-(1-methylethyl)-5-oxo-1H-imidazol-2-yl]-5-ethyl-3-pyridinecarboxylic acid ("imazethapyr"), and (+/−)-2-[4,5-dihydro-4-methyl-4-(1-methylethyl)-5-oxo-1H-imidazol-2-yl]-3-quinolinecarboxylic acid ("imazaquin"); diphenyl ethers such as 5-[2-chloro-4-(trifluoromethyl)phenoxy]-2-nitrobenzoic acid ("acifluorfen"), methyl 5-(2,4-dichlorophenoxy)-2-nitrobenzoate ("bifenox"), and 5-[2-chloro-4-(trifluoromethyl)phenoxy]-N-(methylsulfonyl)-2-nitrobenzamide ("fomasafen"); hydroxybenzonitriles such as 4-hydroxy-3,5-diiodobenzonitrile ("ioxynil") and 3,5-dibromo-4-hydroxybenzonitrile ("bromoxynil"); sulfonylureas such as 2-[[[[(4chloro-6-methoxy-2-pyrimidinyl)amino]carbonyl]amino]sulfonyl]benzoic acid ("chlorimuron"), 2-chloro-N-[[(4-methoxy-6-methyl-1,3,5-triazin-2-yl)amino]carbonyl]benzenesulfonamide (achlorsulfuron"), 2-[[[[[(4,6-dimethoxy-2-pyrimidinyl)amino]carbonyl]amino]sufonyl]methyl]benzoic acid ("bensulfuron"), 2-[[[[(4,6-dimethoxy-2-pyrimidinyl)amino]carbonyl]-amino]sulfonyl]-1-methy-1H-pyrazol-4-carboxylic acid ("pyrazosulfuron"), 3-[[[[(4-methoxy-6-methyl-1,3,5-triazin-2-yl)amino]carbonyl]amino]sulfonyl]-2-thiophenecarboxylic acid ("thifensulfuron"), and 2-(2-chloroethoxy)-N[[(4-methoxy-6-methyl-1,3,5-triazin-2-yl)

amino]carbonyl]benzenesulfonamide ("triasulfuron"); 2-(4-aryloxyphenoxy)alkanoic acids such as (+/−)-2[4-[(6-chloro-2-benzoxazolyl)oxy]phenoxy]propanoic acid (fenoxaprop"), (+/−)-2-[4-[[5-(trifluoromethyl)-2-pyridinyl]oxy]phenoxy]propanoic acid ("fluazifop"), (+/−)-2-[4-(6chloro-2-quinoxalinyl)oxy]phenoxy]propanoic acid ("quizalofop"), and (+/−)-2-[(2,4-dichlorophenoxy)phenoxy]propanoic acid ("diclofop"); benzothiadiazinones such as 3-(1-methylethyl)-1H-2,1,3-benzothiadiazin-4(3H)-one-2,2-dioxide ("bentazone"); 2-chloroacetanilides such as N-(butoxymethyl)-2-chloro-2',6'-diethyacetanilide ("butachlor"); arenecarboxylic acids such as 3,6-dichloro2-methoxybenzoic acid ("dicamba"); and pyridyloxyacetic acids such as [(4-amino-3,5-dichloro-6-fluoro-2-pyridinyl)oxy]acetic acid ("fluroxypyr").

It is apparent that various modifications may be made in the formulations and application of the compounds of the present invention without departing from the inventive concepts herein, as defined in the claims.

We claim:

1. A compound having the formula

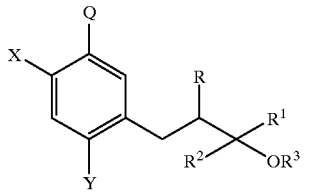

where Q is

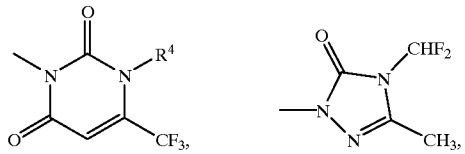

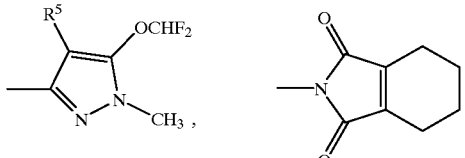

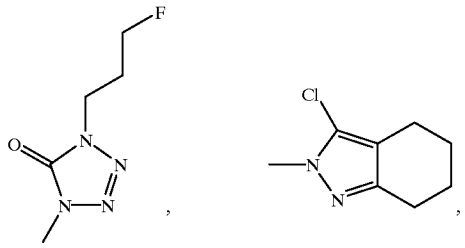

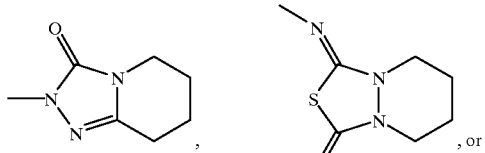

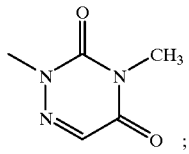

R is hydrogen, halogen, or alkyl;

$R^1$ is hydrogen, cyano, or alkyl;

$R^2$ is hydrogen, or alkyl;

$R^3$ is hydrogen, straight or branched chain alkyl carbonyl, alkoxycarbonyl, alkylaminocarbonyl, or cycloalkylaminocarbonyl;

X is hydrogen or halogen;

Y is halogen, cyano, alkyl, haloalkyl, alkoxy, haloalkoxy, or nitro;

$R^4$ is hydrogen, amino, straight or branched chain alkyl, haloalkyl, cyanoalkyl, alkoxyalkyl, arylalkyl, alkoxycarbonylalkyl, arylalkyl, alkoxycarbonylalkyl, alkenyl, alkynyl, or a salt-forming ion; and $R^5$ is halogen.

2. A compound of claim 1 where Q is 1-substituted-6-trifluoromethyl-2,4(1H,3H)-pyrimidinedion-3-yl.

3. A compound of claim 1 where Q is 4-difluoromethyl-4,5-dihydro-3-methyl-1,2,4-triazol-5(1H)-on-1-yl.

4. A compound of claim 1 where Q is 4-halo-5-difluoromethoxy-1-methylpyrazol-3-yl.

5. A compound of claim 1 where Q is 3,4,5,6-tetrahydrophthalimid-1-yl.

6. A compound of claim 1 where Q is 1,4-dihydro-4-(3-fluoropropyl)-5H-tetrazole-5-on-1-yl.

7. A compound of claim 1 where Q is 3-chloro-4,5,6,7-tetrahydroindazol-2-yl.

8. A compound of claim 1 where Q is 5,6,7,8-tetrahydro-1,2,4-triazolo[4,3-A]pyridin-3(2H)-on-2-yl.

9. A compound of claim 1 where Q is 5,6,7,8-tetrahydro-1H,3H-[1,3,4]thiadiazolo[3,4-a]pyridazineimin-1-yl.

10. A compound of claim 1 where Q is 4-methyl-1,2,4-triazine-3,5-dion-3-yl.

11. A compound of claim 1 where Y and R are chloro; $R^1$ and $R^2$ are hydrogen or methyl; $R^3$ is hydrogen or alkylaminocarbonyl; and X is fluoro.

12. A compound of claim 11 where Q is 1-substituted-6-trifluoromethyl-2,4(1H,3H)-pyrimidinedion-3-yl; and $R^4$ is methyl or amino.

13. A compound of claim 12 where $R^3$ is methylaminocarbonyl.

14. A herbicidal composition comprising a herbicidally effective amount of a compound of claim 1, and a herbicidally compatible carrier therefor.

15. A herbicidal composition comprising an herbicidally effective amount of a compound of claim 1 and an herbicidally effective amount of one or more herbicides selected from the group consisting of glyphosate, 2,4-D, (4-chloro-2-methylphenoxy)-acetic acid, (+/−)-2-(4-chloro-2-methylphenoxy)-propanoic acid, isoproturon, imazapyr, imazamethabenz, imazethapyr, imazaquin, acifluorfen, bifenox, fomasafen, ioxynil, bromoxynil, chlorimuron, chlorsulfuron, bensulfuron, pyrazosulfuron, thifensulfuron, triasulfuron, fenoxaprop, fluazifop, quizalofop, diclofop, bentazone, butachlor, dicamba, and fluroxypyr.

16. A composition of claim 15, and a herbicidally compatible carrier therefor.

17. A method of controlling undesired plant growth, comprising application to the locus where the undesired plants are growing or are expected to grow, a herbicidally effective amount of a composition of claim 14.

18. A method of controlling undesired plant growth, comprising application to the locus where the undesired plants are growing or are expected to grow, a herbicidally effective amount of a composition of claim 15.

* * * * *